(12) United States Patent
Canney

(10) Patent No.: US 11,517,364 B2
(45) Date of Patent: Dec. 6, 2022

(54) METHOD AND SYSTEM FOR DETECTING A FAULT IN AN ELECTRICAL CONNECTION BETWEEN AN ULTRASOUND DEVICE AND A REMOTE CONTROL UNIT

(71) Applicant: CARTHERA, Paris (FR)

(72) Inventor: Michael Canney, Denver, CO (US)

(73) Assignee: CARTHERA, Paris (FR)

( * ) Notice: Subject to any disclaimer, the term of this patent is extended or adjusted under 35 U.S.C. 154(b) by 818 days.

(21) Appl. No.: 16/316,161

(22) PCT Filed: Jul. 6, 2017

(86) PCT No.: PCT/EP2017/066899
§ 371 (c)(1),
(2) Date: Jan. 8, 2019

(87) PCT Pub. No.: WO2018/007500
PCT Pub. Date: Jan. 11, 2018

(65) Prior Publication Data
US 2019/0209228 A1 Jul. 11, 2019

(30) Foreign Application Priority Data
Jul. 8, 2016 (FR) ........................................ 1656611

(51) Int. Cl.
*A61B 18/00* (2006.01)
*A61N 7/00* (2006.01)

(52) U.S. Cl.
CPC ................ *A61B 18/00* (2013.01); *A61N 7/00* (2013.01); *A61B 2018/00178* (2013.01);
(Continued)

(58) Field of Classification Search
CPC .................................................... A61N 1/3605
See application file for complete search history.

(56) References Cited

U.S. PATENT DOCUMENTS

| 4,791,915 A | 12/1988 | Barsotti et al. |
| 2003/0028341 A1 | 2/2003 | Fallon et al. |

(Continued)

FOREIGN PATENT DOCUMENTS

| EP | 1629779 A1 | 3/2006 |
| EP | 2324769 A1 | 5/2011 |

(Continued)

OTHER PUBLICATIONS

The English translation of the Notice of Rejection Reasons issued from the Japanese Patent Office dated Feb. 2, 2021, during prosecution of corresponding application JP 2018-569076.

*Primary Examiner* — Ronald Hupczey, Jr.
(74) *Attorney, Agent, or Firm* — BCF LLP

(57) ABSTRACT

The present invention relates to a pathology treatment apparatus comprising:
an ultrasound generator device (1),
a remote control unit (2) for delivering electricity to the device (1) during at least an activation cycle and determining and controlling the operating parameters thereof, each activation cycle (50) being preceded by a standby cycle,
means (31, 32) of electrical connection between the device (1) and the control unit (2), notable in that the control unit (2) is programmed to detect a fault with the electrical connection between the device (1) and the said control unit (2) during at least a standby cycle.

16 Claims, 4 Drawing Sheets

FIG. 3

(52) U.S. Cl.
CPC ........... *A61B 2018/00642* (2013.01); *A61B 2018/00898* (2013.01); *A61N 2007/0043* (2013.01); *A61N 2007/0047* (2013.01)

(56) References Cited

U.S. PATENT DOCUMENTS

| | | | |
|---|---|---|---|
| 2004/0002652 A1 | 1/2004 | Phelps et al. | |
| 2012/0083717 A1 | 4/2012 | Alleman et al. | |
| 2013/0204316 A1* | 8/2013 | Carpentier | A61B 8/56 607/45 |
| 2014/0171802 A1* | 6/2014 | Kuroiwa | A61B 8/4477 600/459 |
| 2014/0180103 A1* | 6/2014 | Sinelnikov | A61B 8/4494 600/439 |
| 2015/0157299 A1* | 6/2015 | Hopple | A61B 8/58 600/459 |

FOREIGN PATENT DOCUMENTS

| | | |
|---|---|---|
| EP | 2539021 B1 | 2/2016 |
| JP | 2006-095288 A | 4/2006 |

\* cited by examiner

METHOD AND SYSTEM FOR DETECTING A FAULT IN AN ELECTRICAL CONNECTION BETWEEN AN ULTRASOUND DEVICE AND A REMOTE CONTROL UNIT

CROSS-REFERENCE TO RELATED APPLICATIONS

This application is a national phase filing under 35 U.S.C. § 371 of International Application No. PCT/EP2017/066899 filed on Jul. 6, 2017, which claims benefit of priority from French Patent Application No. 1656611 filed Jul. 8, 2016, the contents of which are hereby incorporated by reference in their entirety.

FIELD OF THE INVENTION

The present invention relates to the general technical field of ultrasonic devices—for example intracorporeal or implantable devices—intended to be electrically joined to a remote control unit.

Such devices can in particular be implanted in humans and mammals to assist a practitioner in establishing a diagnosis and/or to treat a pathology.

BACKGROUND OF THE INVENTION

An apparatus for treating brain disorders is known from Document EP 2 539 021. With reference to FIG. 1, such an apparatus is composed of:
- an ultrasonic device 1 made of non-ferromagnetic material,
- a control unit 2 remote from the ultrasonic device 1, and
- means for connecting the ultrasonic device 1 and the control unit 2.

The ultrasonic device 1 is intended to be positioned in a burr hole made in the skull of a patient. It is advantageously compatible with the Magnetic Resonance Imaging (MRI) technique, and comprises:
- a casing 11 composed of walls made of an electrically insulating material,
- at least one transducer 12 positioned in the casing to generate ultrasonic waves for treating a brain disorder,
- fixing means 13 for fixing the casing 11 in the patient's skull,
- one (or more) electrical connection terminal(s) 14 intended to cooperate with connection means.

The control unit 2 is intended to supply the intracorporeal device 1 with electrical energy, and to set its operating parameters.

The connection means are intended to electrically link the ultrasonic device 1 to the control unit 2. They generally comprise:
- one (or more) electrical connection cable(s) 31, one end of which is linked to the control unit, and
- one (or more) transdermal needle(s) 32 joined to the other end of the cable 31.

The operating principle of this apparatus is as follows. Once the ultrasonic device 1 is implanted in the patient's skull, a succession of treatment sessions is provided to said patient for treating the pathology that affects him. At each new treatment session, the intracorporeal device 1 is linked to the control unit 2 via the connection means.

The practitioner links the cable 31 to the control unit 2 and then inserts the needle 32 through the skin of the patient up to the terminal 14 of the ultrasonic device.

Once the end of the needle 32 is connected to the terminal 14, the control unit 2 can be activated to supply the ultrasonic device 1 with electrical energy.

Even if the apparatus described in EP 2 539 021 enables effective treatment of brain disorders, there is currently no technique for informing the practitioner of a possible defect in the electrical junction between the intracorporeal device and the control unit 2. Such an electrical junction defect can cause:
- safety issues for the patient (burns, electric shock, etc.), and/or
- issues in the efficiency of the ultrasonic device concerning the diagnosis and/or the treatment of a pathology.

An aim of the present invention is to provide a method and a system allowing the practitioner to detect a possible defect in the electrical junction between:
- an intracorporeal device 1 implanted in a patient, and
- an external control unit 2.

BRIEF DESCRIPTION OF THE INVENTION

To this end, the invention proposes an apparatus for diagnosis assistance and/or treatment of a pathology comprising:
- an ultrasonic generating device,
- a remote control unit for determining and controlling operating parameters of the device, and providing it with electricity during at least one activation cycle, each activation cycle being preceded by a waiting cycle,
- means for electrically connecting the device and the control unit, remarkable in that the control unit is adapted to detect a defect in the electrical junction between the device and said control unit during at least one waiting cycle.

In the context of the present invention, "electrical junction defect" means a weakness in the electrical connection between the ultrasonic generating device and the probe, this weakness preventing the circulation of an electric current between the ultrasonic generating device and the probe. In other words, a "junction defect" consists of the absence of electrical link between the ultrasonic generating device and the probe.

Preferred but non-limiting aspects of the present invention are as follows:
- the control unit can be programmed:
  - During a waiting cycle:
    - to emit, towards the device, at least one control signal at least at a first instant of the waiting cycle,
    - to acquire at least one feedback signal in response to the emitted control signal,
    - to process the acquired feedback signal in order to detect a defect in the electrical junction between the device and the control unit,
  - During an activation cycle subsequent to the waiting cycle:
    - to emit an activation signal from the device if no electrical junction defect is detected,
    - not to emit the activation signal if an electrical junction defect is detected;
- at least one control signal may consist of a low-power electrical pulse signal emitted at a frequency F1 selected within a range of working frequencies of a transducer of the device;
- the impedance of the device may vary depending on the frequency of the control signal;
- advantageously:

at least a first control signal may consist of an electrical pulse signal emitted at a first frequency F1 selected within a range of working frequencies of a transducer of the device, at least a second control signal may consist of an electrical pulse signal emitted at a second frequency F2 selected outside the range of working frequencies of the transducer;

the control unit can be programmed:
  During a waiting cycle:
    to emit, towards the device, the first control signal at least at a first instant of the waiting cycle and acquire a first feedback signal,
    to emit, towards the device, the second control signal at least at a second instant of the waiting cycle and acquire a second feedback signal,
    to compare the first and second feedback signals with first and second threshold values in order to detect a defect in the electrical junction between the device and the control unit,
  During an activation cycle consecutive to the waiting cycle:
    to emit, towards the device, an activation signal if no electrical junction defect is detected, the activation signal consisting of an electrical pulse signal emitted at the first frequency F1 selected within the range of working frequencies of the transducer, the electric power of the activation signal being greater than the electrical power of the control signals,
    not to emit the activation signal otherwise;

the processing step may comprise a sub-step consisting in comparing the electrical power of each feedback signal with at least one threshold value;

the control unit can be programmed:
  During a waiting cycle:
    to emit a low-power pulse control signal at a frequency F1 selected within a range of working frequencies of the transducer,
    to acquire a response feedback signal,
    to process the feedback signal in order to determine a vibratory or non-vibratory state of the transducer in order to deduce therefrom a possible junction defect,
  During an activation cycle consecutive to the waiting cycle:
    to emit, towards the device, an activation signal if no electrical junction defect is detected, the activation signal consisting of an electrical pulse signal emitted at the first frequency F1 selected within the range of working frequencies of the transducer, the electric power of the activation signal being greater than the electrical power of the control signals,
    not to emit the activation signal, otherwise;

the control unit may comprise a directional coupler for acquiring the feedback signals, said directional coupler being linked upstream of an impedance matching circuit.

The invention also relates to a method for detecting a malfunction of an apparatus for diagnosis assistance and/or treatment of a pathology by applying ultrasounds to a tissue, the apparatus comprising:
an ultrasonic generating device,
a remote control unit for providing electricity to the device and determining and controlling its operating parameters, the control unit being adapted to provide electricity to the device during at least one activation cycle so as to activate said device, each activation cycle being preceded by a waiting cycle,
the device and the control unit being electrically joined via electrical connection means,
remarkable in that the method comprises a control phase implemented during at least one waiting cycle for detecting a defect in the electrical junction between the device and the control unit.

Preferred but non-limiting aspects of the method according to the invention are the following:
the method comprises the following steps:
  During a waiting cycle:
    emitting, by the control unit, at least one control signal at a first instant of the waiting cycle,
    acquiring, by the control unit, at least one feedback signal at a second instant of the waiting cycle,
    processing the feedback signal to obtain information on the quality of the electrical junction between the ultrasonic device and the control unit,
  During an activation cycle subsequent to the waiting cycle, emitting a signal based on the information obtained on the quality of the electrical junction, said signal consisting of:
    an activation signal if the control unit is properly joined to the ultrasonic device,
    an alarm signal if the control unit is not properly joined to the ultrasonic device;

the at least one control signal may consist of a low-power electrical pulse signal emitted at a frequency selected within a range of working frequencies of a transducer of the device;

the impedance of the device may vary depending on the frequency of the control signal;

Advantageously:
  at least a first control signal may consist of an electrical pulse signal emitted at a first frequency selected within a range of working frequencies of a transducer of the device,
  at least a second control signal may consist of an electrical pulse signal emitted at a second frequency selected outside the range of working frequencies of the transducer;

More specifically, the method may comprise the following steps:
  During a waiting cycle:
    emitting, by the control unit, a first low-power pulse control signal at a first frequency selected within a range of working frequencies of the transducer of the ultrasonic device and acquiring, by the control unit, a first response feedback signal,
    emitting, by the control unit, a second low-power pulse control signal at a second frequency selected outside the range of working frequencies of the transducer and acquiring, by the control unit, a second response feedback signal,
    processing the first and second feedback signals to detect a possible junction defect,
  During an activation cycle consecutive to the waiting cycle:
    emitting, by the control unit, an alarm signal if a junction defect is detected,
    emitting, by the control unit, an activation signal otherwise, the activation signal consisting of a high-power electrical pulse signal emitted at the working frequency of the transducer;

the processing step may comprise a sub-step consisting in comparing the electrical power of each feedback signal with at least one threshold value;

Even more specifically, the method may comprise the following steps:
During a waiting cycle:
emitting a low-power pulse control signal at a frequency selected within a range of working frequencies of the transducer,
acquiring a response feedback signal,
processing the feedback signal to detect a possible junction defect, the processing consisting in extracting the peaks from the feedback signal after the end of emission of the control signal in order to deduce therefrom the vibratory or non-vibratory state of the transducer,
During an activation cycle consecutive to the waiting cycle:
emitting an alarm signal if a junction defect is detected,
emitting an activation signal otherwise, the activation signal consisting of a high-power electrical pulsed signal emitted at the frequency of the transducer;

the method may further comprise the following steps:
During the waiting cycle:
emitting, by the control unit, a communication request towards the ultrasonic generating device,
acquiring, by the control unit, a response message emitted by the ultrasonic generating device,
During the activation cycle:
emitting an alarm signal if no response message has been acquired,
emitting an activation signal otherwise.

the method further comprises a monitoring phase implemented during at least one waiting cycle for detecting a defect in the acoustic coupling between the ultrasonic generating device and the tissue;

for the combined detection of a junction defect and of a coupling defect, the method may comprise the following steps:
During a waiting cycle:
emitting, by the control unit, at least one control signal at a first instant of the waiting cycle,
acquiring, by the control unit, at least one feedback signal at a second instant of the waiting cycle,
processing the feedback signal to obtain information on the quality of the electrical junction between the ultrasonic device and the control unit and on the quality of the acoustic coupling between the device and the tissue,
During an activation cycle subsequent to the waiting cycle, emitting a signal based on the information obtained on the quality of the electrical junction and on the information obtained on the quality of the acoustic coupling, said signal consisting of:
an activation signal if the control unit is properly joined to the ultrasonic device and if the apparatus is properly coupled to the tissue,
an alarm signal if the control unit is not properly joined to the ultrasonic device or if the apparatus is not properly coupled to the tissue.

BRIEF DESCRIPTION OF THE DRAWINGS

Other advantages and characteristics of the method according to the invention will become more apparent from the following description of several variants, given by way of non-limiting examples, from the appended drawings in which.

DETAILED DESCRIPTION OF THE INVENTION

Figure 1:
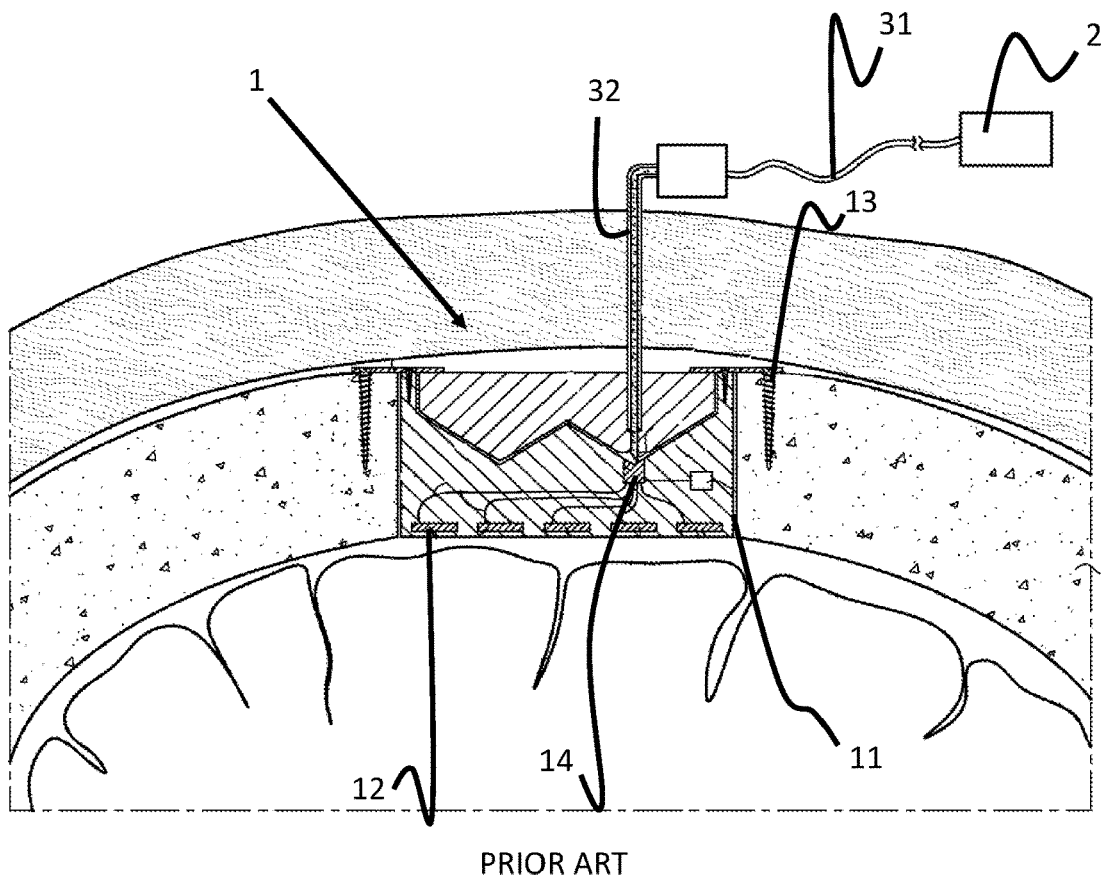
FIG. 1 schematically illustrates an example of an apparatus for treating a brain disorder including an ultrasonic device electrically joined to a remote control unit through connection means (transdermal needle+cable)

Various examples of detection method will now be described with reference to FIGS. 2 to 7. In these different figures, the equivalent elements are designated by the same reference numeral.

This detection method allows a practitioner to check whether the electrical junction between an external control unit and an ultrasonic device implanted in the body of a patient is properly performed.

In the following, the detection method will be described with reference to the apparatus presented in document EP 2 539 021.

However, it is obvious to those skilled in the art that the method according to the invention can be implemented with any type of treatment apparatus including an ultrasonic device—intracorporeal device, implantable device or non-implantable device—to be electrically joined to a remote control unit.

As previously described, the apparatus comprises:
an ultrasonic device 1 comprising a casing 11 in which at least one transducer 12 is housed for the generation of ultrasonic waves,
a remote control unit 2 for supplying the ultrasonic device 1 with electrical energy, and setting its operating parameters,
connection means (transdermal needle+cable) for electrically joining the ultrasonic device 1 and the control unit 2.

This apparatus enables treatment of a brain disorder by implementing several treatment sessions prescribed by the practitioner, each session being composed of a succession of activation cycles each preceded by a waiting cycle.

During a waiting cycle, the ultrasonic device 1 is deactivated for a waiting period (in the order of 975 milliseconds). This deactivation is performed by not supplying the ultrasonic device 1 with electrical energy.

When the waiting period has expired, an activation cycle is implemented. The activation of the ultrasonic device 1 is performed by supplying it with electrical energy during an activation period (in the order of 25 milliseconds). This electrical energy is advantageously emitted by the control unit 2 at a working frequency of the transducer 12. The transducer 12 generates ultrasonic waves in the direction of the brain region located just below the ultrasonic device 1.

When the activation period has expired, a new waiting cycle is implemented, and so on until the end of the session.

The detection method described in the following proposes to use the waiting cycle preceding each activation cycle in order to detect the quality of the electrical junction between the ultrasonic device 1 and the control unit 2.

1. Method for Detecting the Quality of an Electrical Junction Between the Ultrasonic Device and the Control Unit Different embodiments of the detection method will now be described in more detail.

It is assumed in the following that the ultrasonic device 1 has been implanted in the skull of the patient and that the practitioner has electrically joined the ultrasonic device 1 to the control unit 2.

Figure 2:
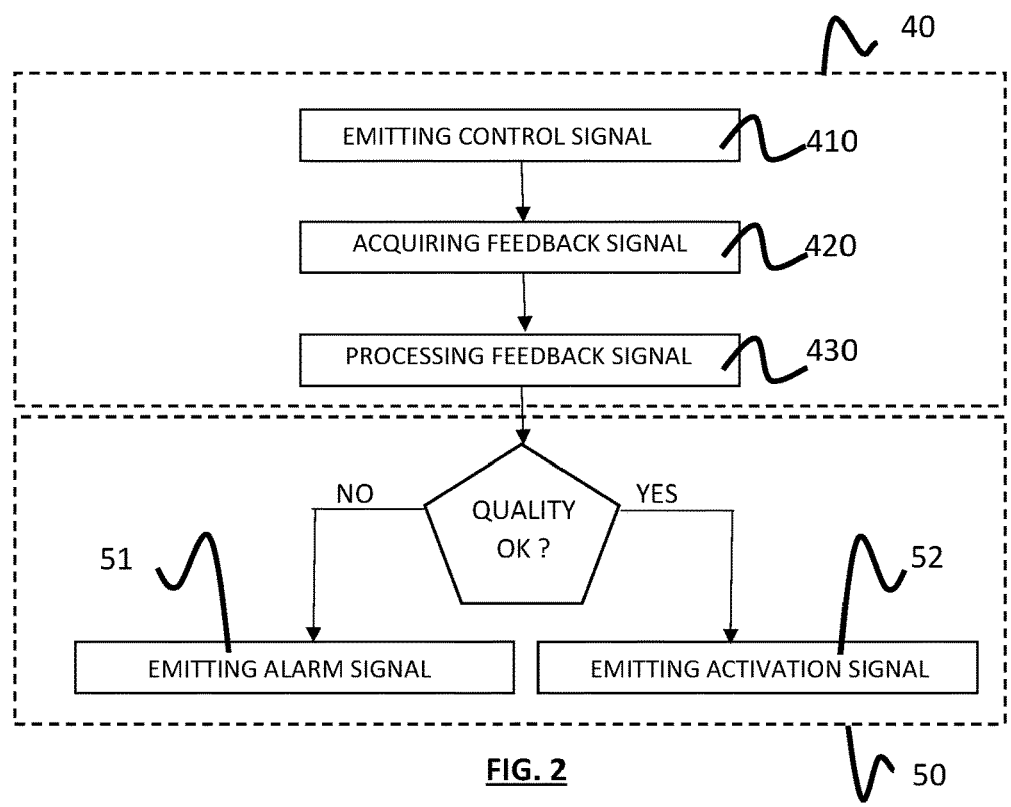
FIG. 2 illustrates steps of a method for detecting a defect in the electrical junction between the device and the control unit.

With reference to FIG. 2, the detection method comprises the following steps:

During each waiting cycle 40:
- emitting 410, by the control unit 2, at least one control signal at a first instant of the waiting cycle 40,
- acquiring 420, by the control unit 2, at least one feedback signal at a second instant of the waiting cycle 40,
- processing 430 the feedback signal to obtain information on the quality of the electrical junction between the ultrasonic device 1 and the control unit 2, During each activation cycle 50, emitting 51, 52 a signal based on the information obtained on the quality of the electrical junction, said signal consisting of:
- an activation signal if the control unit 2 is properly joined to the ultrasonic device 1,
- an alarm signal if the control unit 2 is not properly joined to the ultrasonic device 1.

Each control signal is emitted at a low electrical energy with respect to the activation signal (in the order of 1% of the energy required for the treatment). This allows avoiding the risks of heating the patient during the phase of controlling the quality of the electrical junction between the ultrasonic device 1 and the control unit 2, in particular in the case of a faulty junction. In particular, in the event of a short-circuit at the transdermal needle by contact of its poles with a tissue, the emission of the activation signal can cause an electric shock. Although this electric shock is not necessarily dangerous, it can be painful for the patient and cause the burn of a small area of tissue in the scalp.

Thus, the method according to the invention allows the practitioner to check the quality of the electrical junction between the ultrasonic device 1 and the control unit 2 prior to each activation phase. This thereby ensures the effectiveness of the treatment during each activation cycle.

Different types of faulty junction can be encountered:
- The cable 31 may not be electrically linked to the control unit 2,
- The transdermal needle 32 may not be electrically linked to the terminal 14; in this case, the tip of the needle 32 is in contact:
  - either with an electrical insulator (needle 32 having not passed through the insulating material layer covering the terminal 14),
  - or with an electrical conductor (skin of the skull or fluid circulating in the patient's skull).

The two variants of the method described in the following allow detecting these different types of faulty electrical junction.

1.1. First Embodiment

Figure 3:
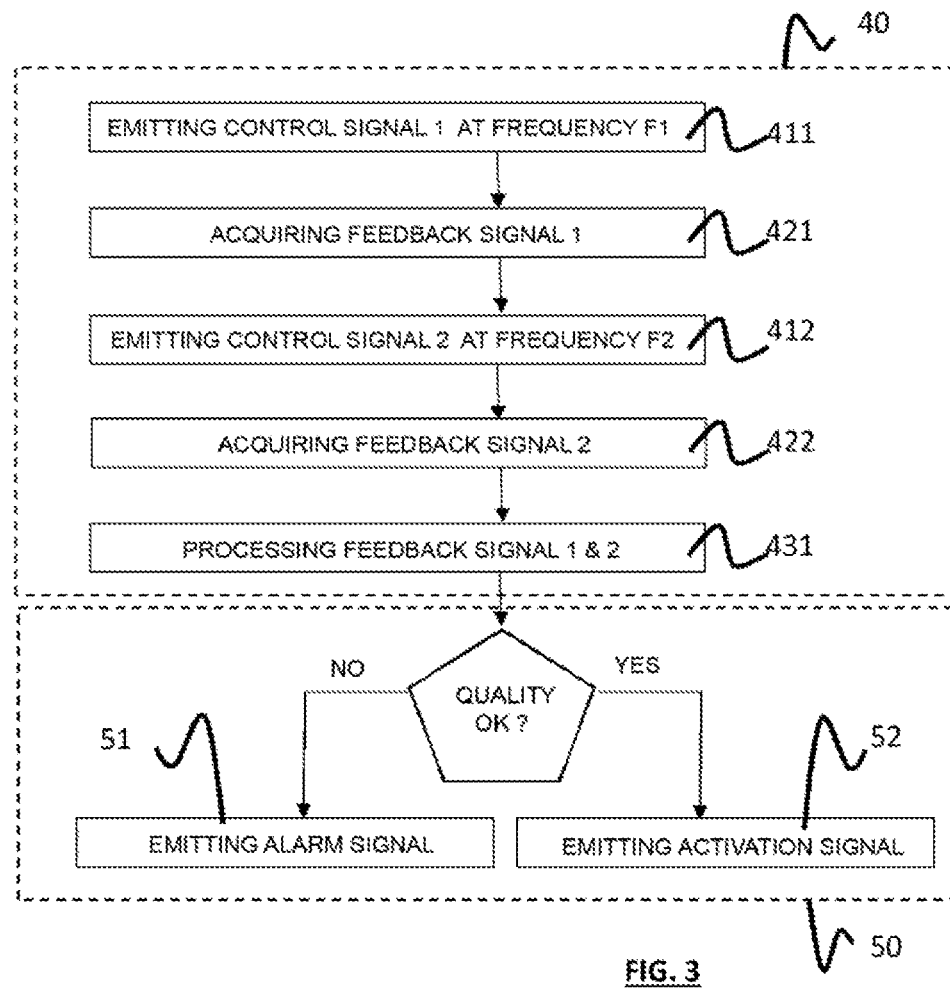
FIG. 3 illustrates a first variant of the detection method of FIG. 2.
Figure 4:
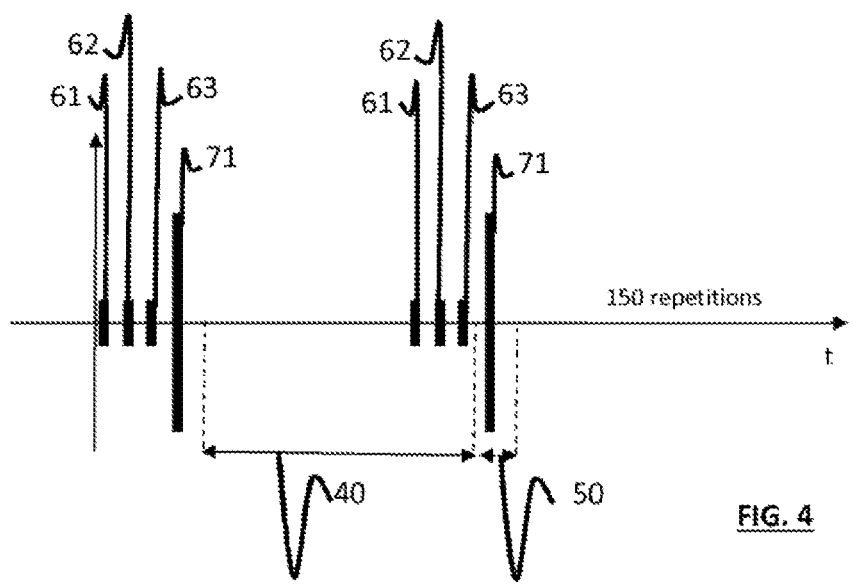
FIG. 4 illustrates a first example of a detection strategy according to the first variant of the method.

In a first variant illustrated in FIGS. 3 and 4, the method uses a multi-frequency approach. Particularly, in this first variant, control signals are emitted at two distinct frequencies.

The fact of emitting control signals at different frequencies allows improving the reliability of the method for detecting faulty electrical junctions.

Indeed, if a single frequency is used with a tolerance on the reflected power, then:
- the power reflected in the case where the needle 32 is properly linked to the ultrasonic device 1, and
- the power reflected in the case where the tip of the needle 32 is in contact with a tissue (which is conductive)
- may be similar, so that it is difficult to differentiate a proper electrical junction from a faulty electrical junction in which the needle is simply in a conductive medium (the two poles which are located at the tip of the needle being then short-circuited).

The multi-frequency approach—i.e. the use of control signals at two distinct frequencies—allows removing this ambiguity. Indeed, the ultrasonic device has the particularity of having impedance varying depending on the frequency of the electrical signal applied thereto.

Advantageously, the control signals emitted during the waiting cycle 40 are electrical pulse currents, the frequencies selected for the emission of said control signals being:
- A first frequency F1 (for example in the order of 1.05 MHz) selected within a range of working frequencies—such as a resonance frequency—of the transducer 12,
- A second frequency F2 distinct from the first frequency F1 selected outside the range of working frequencies of the transducer 12, so that most of the control signal emitted at the frequency F2 by the control unit 2 is reflected towards it;

With reference to FIG. 3, the method may comprise the following steps:

During the waiting cycle 40:
- emitting 411 a first low-power pulse control signal at a first frequency F1 selected within a range of working frequencies of the transducer 12 of the ultrasonic device 1, and acquiring 421 a first response feedback signal,
- emitting 412 a second low-power pulse control signal at a second frequency F2 selected outside the range of working frequencies of the transducer 12, and acquiring 422 a second response feedback signal,
- processing 431 the first and second feedback signals to detect a possible junction defect, During the activation cycle 50:
- emitting 51 an alarm signal if a junction defect is detected,
- emitting 52 an activation signal otherwise, the activation signal consisting of a high-power electrical pulse signal emitted at the working frequency F1 of the transducer 12.

Advantageously, acquiring the first and second feedback signals may consist in measuring the electrical powers of said feedback signals, for example by using a directional coupler. This allows limiting the complexity of the control unit.

In addition to the electrical junction defects between the ultrasonic device 1 and the control unit 2, the multifrequency approach can allow detecting the manufacturing defects of the transdermal needle 32, such as a short-circuit at the poles of the needle 32, for example by implementing the method illustrated in FIG. 3 prior to insertion of the needle 32 in the patient.

FIG. 4 illustrates an exemplary strategy that can be used to detect a junction defect by implementing the first variant of the method according to the invention.

Three control signals 61, 62, 63—each consisting of a low-power electrical pulse of a 100 microseconds duration—are emitted towards the ultrasonic device during each waiting cycle 40:
- a first pulse 61 emitted at the frequency F2 selected outside the range of working frequencies of the transducer 12,
- a second pulse 62 emitted at the frequency F1 selected within the range of working frequencies of the transducer 12,
- a third pulse 63 emitted at the frequency F2.

First, second and third feedback signals are acquired in response to the emission of the first, second and third pulses 61, 62, 63.

These first, second and third feedback signals are compared with threshold values contained in a memory of the control unit 2. This comparison allows determining whether the control unit 2 is properly joined to the ultrasonic device 1, or whether there is a defect in the electrical junction.

If the control unit 2 is properly joined to the ultrasonic device 1, an activation signal 71 at the frequency F1, of high-power (i.e. of power greater than the power of the control signals) and of a 23.8 microseconds duration, is emitted towards the ultrasonic device 1 during each activation cycle 50. The emission of the activation signal 71 induces the generation of ultrasonic waves allowing treatment of the patient.

The waiting and activation cycles 40, 50 are then repeated a plurality of times (150 times in the example illustrated in FIG. 4).

The table below illustrates how the comparison of two feedback signals $P_{R1}$, $P_{R2}$ (acquired in response to the emission of two control signals emitted at frequencies F1 and F2) with threshold values $S_1$, $S_2$ allows determining whether the electrical junction between the ultrasonic device 1 and the control unit 2 is proper or not.

The electrical junction is considered as proper if first and second conditions (relating to the comparison of the feedback signals $P_{R1}$, $P_{R2}$ with the threshold values $S_1$, $S_2$) are met in combination:
- the first condition on the feedback signal $P_{R1}$ is met if the measured electrical power is greater than the threshold value $S_1$,
- the second condition on the feedback signal $P_{R2}$ is met if the measured electrical power is lower than the threshold value $S_2$.

If one and/or the other of the first and second conditions is (are) not met, then the electrical junction between the control unit and the ultrasonic device is faulty.

| | Conditions | F2: 0.6 MHz $S_2 = 100$ | F1: 1.05 MHz $S_1 = 210$ |
|---|---|---|---|
| 1 | Junction to the control unit: NO Junction to the implant: NO | $P_{R2} = 24$ $P_{R2} < S_2$ => OK | $P_{R1} = 57$ $P_{R1} < S_1$ => ALARM |
| 2 | Junction to the control unit: YES Junction to the implant: NO Tip of the needle in an insulating medium | $P_{R2} = 30$ $P_{R2} < S_2$ => OK | $P_{R1} = 63$ $P_{R1} < S_1$ => ALARM |
| 3 | Junction to the control unit: YES Junction to the implant: NO Tip of the needle in a conductive medium | $P_{R2} = 107$ $P_{R2} > S_2$ => ALARM | $P_{R1} = 193$ $P_{R1} < S_1$ => ALARM |
| 4 | Junction to the control unit: YES Junction to the implant: YES Transducer in acoustic contact with a conductive medium or the tissue | $P_{R2} = 79$ $P_{R2} < S_2$ => OK | $P_{R1} = 257$ $P_{R1} > S_1$ => OK |
| 5 | Junction to the control unit: YES Junction to the implant: YES Transducer in the air, NOT in acoustic contact with a conductive medium or the tissue | $P_{R2} = 57$ $P_{R2} < S_2$ => OK | $P_{R1} = 212$ $P_{R1} > S_1$ => OK |

Case No. 5 is representative of a situation in which the electrical junction between the ultrasonic device 1 and the control unit 2 is proper, but wherein the transducer 12 is not in contact with the tissue to be treated. Those skilled in the art will appreciate that the addition of a third condition (associated with the comparison of the feedback signal $P_{R1}$ with a third threshold value $S_3$ (for example equal to 230) could allow detecting this anomaly. The reader will appreciate that values $P_{R1}$, $P_{R2}$ correspond to raw values obtained from an analog-to-digital converter.

In the context of the example above, they have not been converted into power values, and the thresholds $S_1$, $S_2$ mentioned above correspond to an arbitrary scale of the power levels.

Of course, the values $P_{R1}$, $P_{R2}$ could be converted into power values, for example by using a quadratic or polynomial function determined by a calibration process of the apparatus according to the invention.

1.2. Second Embodiment

Figure 7:
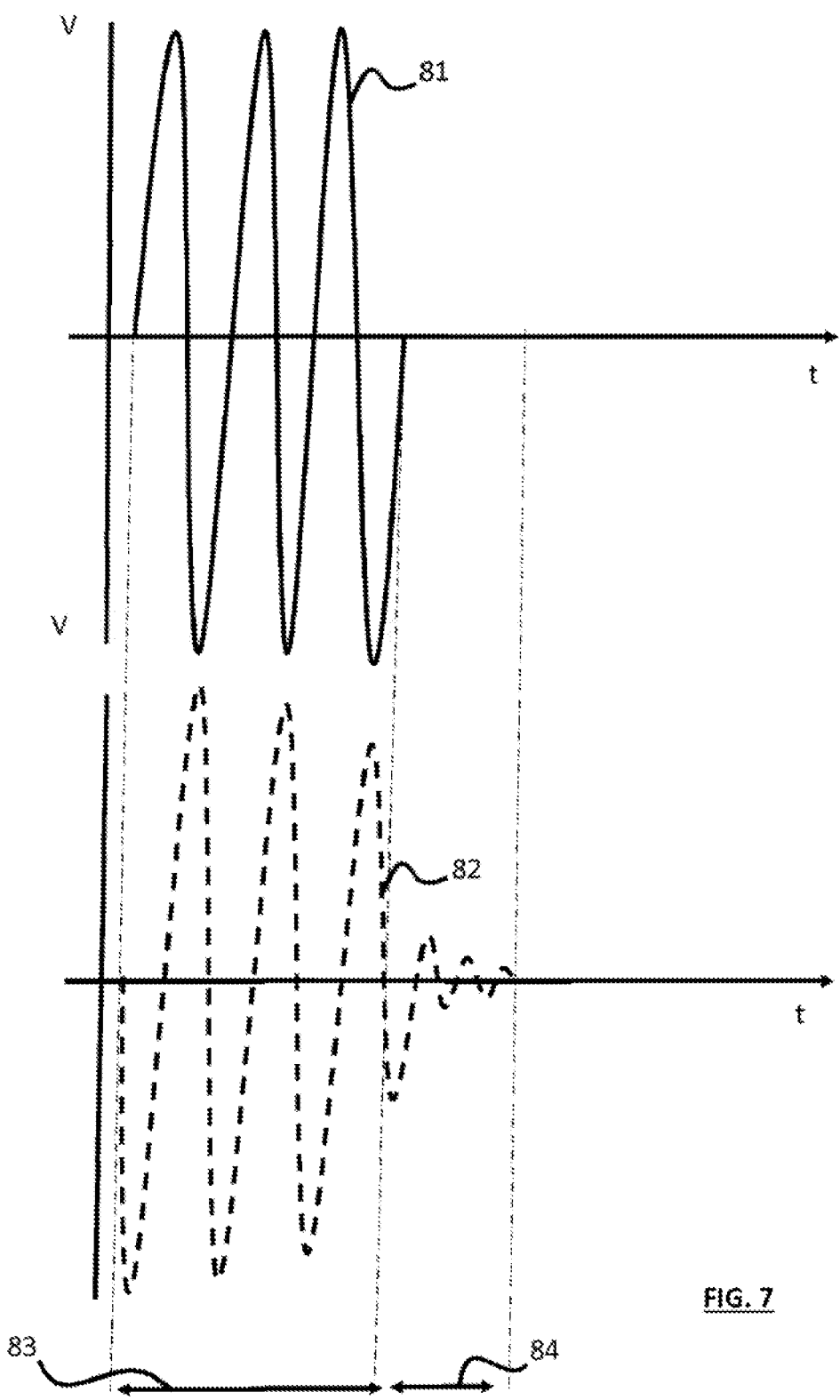
FIG. 7 is a voltage curve as a function of time.

In a second variant embodiment, the method uses a vibratory approach. The vibratory approach is based on the fact that the transducer 12 is a resonant element. When such a resonant element is excited by an electrical pulse emitted at a frequency selected in its working range, it continues to vibrate even after the end of the excitation. FIG. 7 illustrates this phenomenon in the case of a transducer 12 excited by an activation signal 81 during an activation period 83. It is observed that the signal 82 reflected by the transducer 12 continues to vibrate for a non-zero period 84 after the end of the excitation.

This "residual" vibration can be measured by using several techniques:
- either by directly measuring the voltage sent to the transducer 12, which requires that the voltage signal is digitized at a frequency greater than or equal to twice the excitation frequency (Nyquist limit); this technique requires the integration of a high-speed digitizer in the control unit,
- or by measuring the voltage reflected by the transducer 12; this technique requires the integration of a Root Mean Square value (RMS value) converter or of a peak detector for identifying peaks of the reflected voltage but eliminates the need to use a high-speed digitizer.

The signature of the feedback signal is unique to the ultrasonic device 1 and does not occur when the needle 32 is placed in a conductive material such as saline solution.

Figure 5:
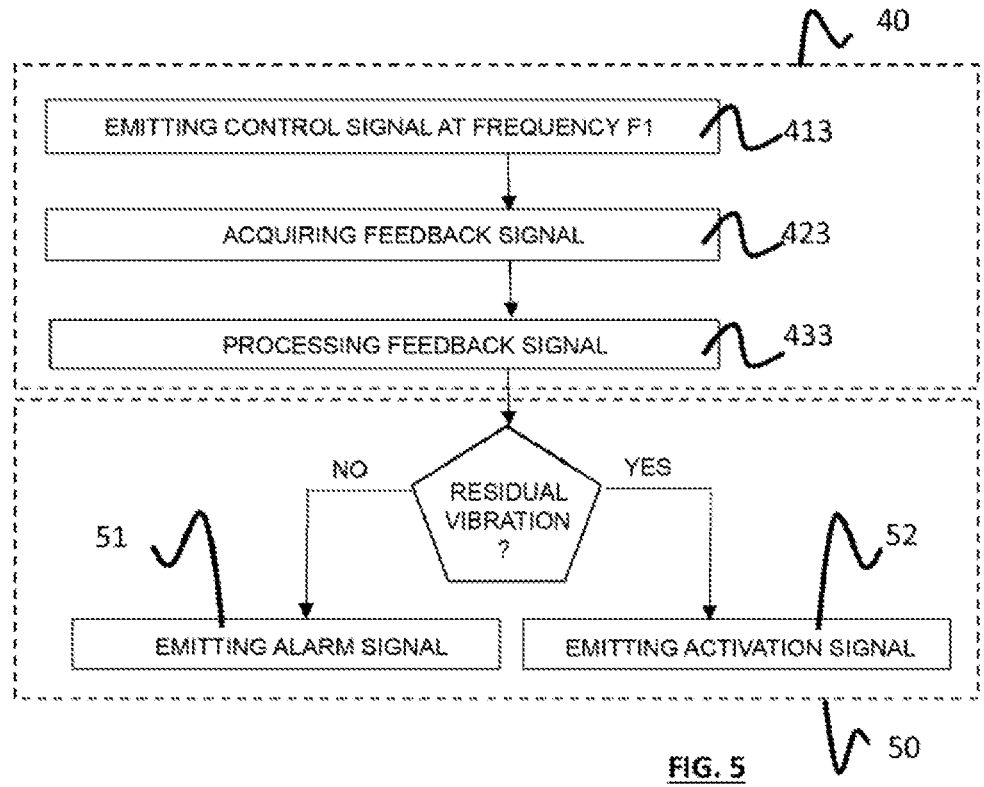
FIG. 5 illustrates a second variant of the detection method of FIG. 2, FIG. 6 schematically illustrates an example of a control unit for implementing the method according to the invention.

With reference to FIG. 5, the method may comprise the following steps:

During each waiting cycle 40:

emitting 413 a low-power pulse control signal at a frequency F1 selected within a range of working frequencies of the transducer 12, acquiring 423 a response feedback signal, processing 433 the feedback signal to detect a possible junction defect, the processing consisting in extracting the peaks from the feedback signal after the end of emission of the control signal in order to deduce therefrom the (vibratory or non-vibratory) state of the transducer 12, During each activation cycle 50:

emitting 51 an alarm signal if a junction defect is detected, emitting 52 an activation signal otherwise, the activation signal consisting of a high-power electrical pulse signal emitted at the frequency F1 of the transducer 12.

2. Control Unit

Figure 6:
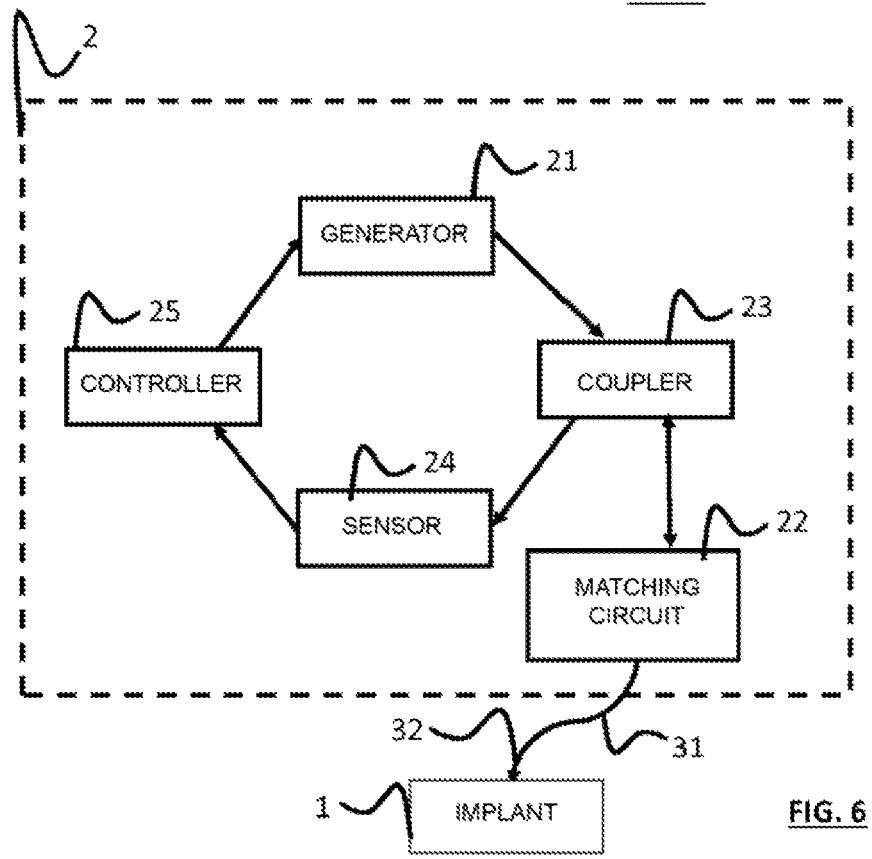

Referring to FIG. 6 which illustrates the control unit 2 of an exemplary apparatus for implementing the method described above.

The control unit 2 comprises:

an electric power supply generator 21 for supplying the ultrasonic device with electrical energy, an impedance matching circuit 22 for optimizing the electrical energy transfer between the generator and the ultrasonic device, a bidirectional coupler 23 between the generator 21 and the impedance matching circuit 22, a sensor 24 downstream of the coupler for extracting, from the signals received from the coupler 23, an electrical power value, a controller 25 for processing the signals coming from the sensor 24 and informing the practitioner of the state of the electrical junction between the ultrasonic device 1 and the control unit 2.

The bidirectional coupler 23 allows acquiring the feedback signals. More specifically, the coupler 23 allows measuring the signals reflected by the ultrasonic device 1, and the connection means (cable 31/needle 32). The bidirectional coupler 23 is for example the ZFBDC20-61 HP+ model from the Mini-Circuits® company, used in combination with a low-cost analog-to-digital converter such as the Picoscope model 3206B from the Pico-Technology® company. Advantageously, the bidirectional coupler 23 is positioned upstream of the impedance matching circuit 22; this allows simplifying the processing of the feedback signals to extract therefrom the reflected electrical power.

The operating principle of the control unit 2 is as follows. During one (or each) waiting cycle 40, the controller 25 orders the generator 21 to emit a low-power control signal. The control signal generated by the generator 21 passes through the bidirectional coupler 23 and the impedance matching circuit 22. It is emitted towards the ultrasonic device 1 via the electrical connection means (cable 31+needle 32).

The bidirectional coupler 23 acquires a feedback signal (or several feedback signals). More specifically, the bidirectional coupler 23 measures the radiofrequency signal reflected by the intra-ultrasonic body device 1, the connection means 31, 32, or the absence of such a radiofrequency signal.

The feedback signal acquired by the bidirectional coupler 23 is transmitted to the sensor 24 that processes it to extract therefrom an electric power value. This electrical power value is transmitted to the controller 25 that compares it to one (or more) threshold value(s) in order to detect a possible electrical junction defect.

If no junction defect is detected, the controller 25 orders the generator 21 to emit a high-power activation signal at the frequency F1 to induce the generation of ultrasonic waves by the transducer 12 of the ultrasonic device 1.

If a junction defect is detected, the controller 25 emits an alert signal to warn the practitioner of said defect, for example by emitting a sound and/or visual stimulus on an interface of the control unit 2 (the interface may comprise a screen and/or a speaker).

Thus, the present invention proposes a solution to the problem of detecting defects in the junction between an implantable ultrasonic device and a remote control unit. Indeed, the device allows detecting a "break" in the connection circuit.

The present invention also allows, as described above, detecting a defect in the acoustic coupling between the treatment (or imaging) apparatus and the tissue to be treated (or imaged), for example by detecting an impedance variation of the transducer(s). This impedance variation may be due to a defect in acoustic contact between the transducer and the tissue. An impedance variation of the transducer may also result from a defect of the transducer itself, for example a short-circuit or an open circuit. When the present invention allows detecting both an electrical junction defect and an acoustic coupling defect, the method can comprise the following steps:

During a waiting cycle:

emitting, by the control unit, at least one control signal at a first instant of the waiting cycle, acquiring, by the control unit, at least one feedback signal at a second instant of the waiting cycle, processing the feedback signal to obtain information on the quality of the electrical junction between the ultrasonic device and the control unit and on the quality of the acoustic coupling between the apparatus and the tissue, During an activation cycle (50) subsequent to the waiting cycle, emitting a signal based on the information obtained on the quality of the electrical junction and on the information obtained on the quality of the acoustic coupling, said signal consisting of:

an activation signal if the control unit is properly joined to the ultrasonic device and if the apparatus is properly coupled to the tissue, an alarm signal if the control unit is not properly joined to the ultrasonic device or if the apparatus is not properly coupled to the tissue.

The reader will understand that several modifications can be made to the invention described above without physically departing from the new teachings and advantages described herein.

For example, the method according to the invention can be used with treatment apparatuses other than the one described in document EP 2 539 021.

Also in the foregoing description, the impedance matching circuit has been described as being integrated to the control unit. Alternatively, the impedance matching circuit can be integrated to the ultrasonic device.

In addition, other electrical signals (electrical control signals or power supply signals of the ultrasonic device) can be emitted by the control unit during the waiting cycle. For example, in a variant of the invention, the ultrasonic device comprises a demultiplexer connected to a plurality of transducers. This demultiplexer enables the sequential activation of the transducers (or the simultaneous activation of some transducers selected among the plurality of transducers). In this case, the control unit can be programmed to interrogate the demultiplexer during one or more waiting cycle(s) in order to check that it is responding (bidirectional digital communication). To this end, the method may comprise the following additional steps:

During one (or each) waiting cycle:
emitting, by the control unit, a communication request towards the ultrasonic generating device,
acquiring, by the control unit, a response message emitted by the ultrasonic generating device,
During the activation cycle:
emitting an alarm signal if no response message has been acquired.

These additional steps can be implemented beforehand, or simultaneously with the steps relating to the detection of an electrical junction defect.

Consequently, all modifications of this type are intended to be incorporated within the scope of the appended claims.

The invention claimed is:

1. A method for detecting a malfunction of an apparatus for diagnosis assistance and/or treatment of a pathology by applying ultrasounds on a tissue, the apparatus comprising:
an ultrasound generator device implanted in a patient, and
a control unit for providing electricity to the ultrasound generator device and for determining and controlling its operating parameters, the control unit being adapted to provide electricity to the ultrasound generator device during at least one activation cycle so as to activate said ultrasound generator device, said at least one activation cycle being preceded by at least one standby cycle,
the ultrasound generator device and the control unit being electrically joined via an electrical junction,
wherein the method comprises a control phase implemented during the at least one standby cycle for detecting a fault with the electrical junction between the ultrasound generator device and the control unit, said fault with the electrical junction consisting of the absence of electrical link between the ultrasound generator device and the control unit, and
wherein the method comprises the following steps:
during the at least one standby cycle:
emitting, by the control unit, at least one control signal at a first instant of the standby cycle, wherein the at least one control signal consists of a low-power electrical pulse signal emitted at a frequency F1 selected within a range of working frequencies of a transducer of the ultrasound generator device,
acquiring, by the control unit, at least one feedback signal at a second instant of the standby cycle, and
processing the at least one feedback signal to obtain information on the quality of the electrical junction between the ultrasound generator device and the control unit; and
during the at least one activation cycle, subsequent to the at least one standby cycle, emitting a signal based on the information obtained on the quality of the electrical junction, said signal comprising an alarm signal if the control unit is not properly joined to the ultrasound generator device.

2. The method according to claim 1, wherein the impedance of the ultrasound generator device varies depending on the frequency of the at least one control signal.

3. The method according to claim 1, wherein the at least one control signal comprises:

a first control signal, wherein the first control signal consists of an electrical pulse signal emitted at the frequency F1, and
a second control signal, wherein the second control signal consists of an electrical pulse signal emitted at a second frequency F2 selected outside the range of working frequencies of the transducer.

4. The method according to claim 3, wherein the method comprises the following steps:
during the at least one standby cycle:
emitting, by the control unit, the first control signal, and acquiring, by the control unit, a first response feedback signal,
emitting, by the control unit, the second control signal, and acquiring, by the control unit, a second response feedback signal, and
processing the first and second response feedback signals to detect a possible junction defect.

5. The method according to claim 1, further comprising comparing the electrical power of each feedback signal of the at least one feedback signal with at least one threshold value.

6. The method according to claim 1, wherein the processing the at least one feedback signal comprises:
extracting the peaks from the at least one feedback signal after the end of emission of the at least one control signal in order to deduce therefrom the vibratory or non-vibratory state of the transducer.

7. The method according to claim 6, which further comprises the following steps:
during the at least one standby cycle:
emitting, by the control unit, a communication request towards the ultrasound generator device, and
during the at least one activation cycle:
emitting the alarm signal if no response message has been acquired during the standby cycle.

8. The method according to claim 1, which further comprises a monitoring phase implemented during the at least one standby cycle for detecting a defect in the acoustic coupling between the ultrasound generator device and the tissue.

9. The method according to claim 8, which comprises the following steps:
during the at least one standby cycle:
processing the feedback signal to obtain information on the quality of the acoustic coupling between the apparatus and the tissue, and
during the at least one activation cycle subsequent to the at least one standby cycle,
emitting the alarm signal if the apparatus is not properly coupled to the tissue.

10. An apparatus for diagnosis assistance and/or treatment of a pathology comprising:
an ultrasound generator device configured to be implanted in a patient, and
a control unit for providing electricity to the ultrasound generator device and for determining and controlling operating parameters of the ultrasound generator device, the control unit being adapted to provide electricity to the ultrasound generator device during at least one activation cycle so as to activate said ultrasound generator device, said at least one activation cycle being preceded by at least one standby cycle, the ultrasound generator device and the control unit being electrically joined via an electrical junction,
wherein the control unit is programmed to detect, during a control phase implemented during the at least one standby cycle, a fault with the electrical junction between the ultrasound generator device and said control unit, and wherein detecting the fault comprises:

during the at least one standby cycle:
- emitting, by the control unit, at least one control signal at a first instant of the standby cycle, wherein the at least one control signal consists of a low-power electrical pulse signal emitted at a frequency F1 selected within a range of working frequencies of a transducer of the ultrasound generator device,
- acquiring, by the control unit, at least one feedback signal at a second instant of the standby cycle, and
- processing the at least one feedback signal to obtain information on the quality of the electrical junction between the ultrasound generator device and the control unit; and during the at least one activation cycle, subsequent to the at least one standby cycle, emitting a signal based on the information obtained on the quality of the electrical junction, said signal comprising an alarm signal if the control unit is not properly joined to the ultrasound generator device.

11. The apparatus according to claim 10, wherein the impedance of the ultrasound generator device varies depending on the frequency of the at least one control signal.

12. The apparatus according to claim 10, wherein the at least one control signal comprises:
- a first control signal, wherein the first control signal consists of an electrical pulse signal emitted at the frequency F1, and
- a second control signal, wherein the second control signal consists of an electrical pulse signal emitted at a second frequency F2 selected outside the range of working frequencies of the transducer.

13. The apparatus according to claim 10, wherein the at least one feedback signal comprises a first feedback signal and a second feedback signal, and wherein the control unit is programmed:

during the at least one standby cycle:
- to compare the first and second feedback signals with first and second threshold values in order to detect a defect in the electrical junction between the ultrasound generator device and the control unit, and during the at least one activation cycle consecutive to the at least one standby cycle:
- to emit, towards the ultrasound generator device, an activation signal if no electrical junction defect is detected, the activation signal consisting of an electrical pulse signal emitted at the frequency F1, the electric power of the activation signal being greater than the electrical power of the at least one control signal, or
- not to emit the activation signal otherwise.

14. The apparatus according to claim 10, wherein the control unit is programmed to compare the electrical power of each of the at least one feedback signal with at least one threshold value.

15. The apparatus according to claim 10, wherein the control unit is programmed:

during the at least one standby cycle:
- to process the at least one feedback signal in order to determine a vibratory or non—vibratory state of the transducer in order to deduce therefrom a possible junction defect, and during the at least one activation cycle consecutive to the at least one standby cycle:
- to emit, towards the ultrasound generator device, the activation signal if no electrical junction defect is detected, the activation signal consisting of an electrical pulse signal emitted at the frequency F1, the electric power of the activation signal being greater than the electrical power of the at least one control signal, or
- not to emit the activation signal, otherwise.

16. The apparatus according to claim 10, wherein the control unit comprises a directional coupler for acquiring the at least one feedback signal, said directional coupler being linked upstream of an impedance matching circuit.

* * * * *